United States Patent
LeBoeuf et al.

(10) Patent No.: US 9,750,462 B2
(45) Date of Patent: Sep. 5, 2017

(54) MONITORING APPARATUS AND METHODS FOR MEASURING PHYSIOLOGICAL AND/OR ENVIRONMENTAL CONDITIONS

(71) Applicant: Valencell, Inc., Raleigh, NC (US)

(72) Inventors: Steven Francis LeBoeuf, Raleigh, NC (US); Jesse Berkley Tucker, Knightdale, NC (US); Michael Edward Aumer, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 314 days.

(21) Appl. No.: 14/166,365

(22) Filed: Jan. 28, 2014

(65) Prior Publication Data
US 2014/0140567 A1 May 22, 2014

Related U.S. Application Data

(63) Continuation of application No. 12/711,736, filed on Feb. 24, 2010, now abandoned.
(Continued)

(51) Int. Cl.
*A61B 5/00* (2006.01)
*G06F 19/00* (2011.01)
(Continued)

(52) U.S. Cl.
CPC .............. *A61B 5/7221* (2013.01); *A61B 5/00* (2013.01); *A61B 5/0013* (2013.01);
(Continued)

(58) Field of Classification Search
None
See application file for complete search history.

(56) References Cited

U.S. PATENT DOCUMENTS

| | | | |
|---|---|---|---|
| 3,595,219 A | 7/1971 | Friedlander et al. | |
| 4,240,882 A | 12/1980 | Ang et al. | |

(Continued)

FOREIGN PATENT DOCUMENTS

| CN | 101212927 A | 7/2008 |
|---|---|---|
| CN | 201438747 U | 4/2010 |

(Continued)

OTHER PUBLICATIONS

Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.

(Continued)

*Primary Examiner* — Lori A. Clow
*Assistant Examiner* — Marie Archer
(74) *Attorney, Agent, or Firm* — Myers Bigel, P.A.

(57) ABSTRACT

A monitoring apparatus includes a wearable electronic device having an audio port and a headset having at least one earbud, at least one physiological and/or environmental sensor, and circuitry that processes signals produced by the at least one physiological and/or environmental sensor and transmits the processed signals to the electronic device via the audio port. The headset may include a microphone in audio communication with the electronic device via the audio port, and the circuitry modulates audio signals produced by the microphone and signals produced by the at least one physiological and/or environmental sensor for transmission to the electronic device via the audio port. The circuitry may power the at least one physiological and/or environmental sensor via power supplied by the electronic device through the audio port and may include a processor that coordinates collection, modulation, and/or transmission (Continued)

of signals produced by the at least one physiological and/or environmental sensor.

4 Claims, 7 Drawing Sheets

Related U.S. Application Data

(60) Provisional application No. 61/208,567, filed on Feb. 25, 2009, provisional application No. 61/208,574, filed on Feb. 25, 2009, provisional application No. 61/212,444, filed on Apr. 13, 2009, provisional application No. 61/274,191, filed on Aug. 14, 2009.

(51) Int. Cl.
| | |
|---|---|
| A61B 5/024 | (2006.01) |
| H04R 1/10 | (2006.01) |
| A61B 5/0205 | (2006.01) |
| A61B 5/11 | (2006.01) |
| A61B 5/1455 | (2006.01) |
| A61B 5/0476 | (2006.01) |
| A61B 5/16 | (2006.01) |
| F21V 8/00 | (2006.01) |
| A61B 5/021 | (2006.01) |
| A61B 5/08 | (2006.01) |
| A61B 5/01 | (2006.01) |
| A61B 5/145 | (2006.01) |
| A61B 5/026 | (2006.01) |
| A61B 5/0295 | (2006.01) |
| A61B 5/091 | (2006.01) |

(52) U.S. Cl.
CPC .......... *A61B 5/0022* (2013.01); *A61B 5/0024* (2013.01); *A61B 5/0059* (2013.01); *A61B 5/0082* (2013.01); *A61B 5/0084* (2013.01); *A61B 5/01* (2013.01); *A61B 5/021* (2013.01); *A61B 5/0205* (2013.01); *A61B 5/02055* (2013.01); *A61B 5/0261* (2013.01); *A61B 5/02427* (2013.01); *A61B 5/02433* (2013.01); *A61B 5/0476* (2013.01); *A61B 5/0816* (2013.01); *A61B 5/11* (2013.01); *A61B 5/1107* (2013.01); *A61B 5/1118* (2013.01); *A61B 5/1455* (2013.01); *A61B 5/14532* (2013.01); *A61B 5/14551* (2013.01); *A61B 5/165* (2013.01); *A61B 5/418* (2013.01); *A61B 5/486* (2013.01); *A61B 5/4812* (2013.01); *A61B 5/4845* (2013.01); *A61B 5/4848* (2013.01); *A61B 5/4866* (2013.01); *A61B 5/4875* (2013.01); *A61B 5/4884* (2013.01); *A61B 5/6803* (2013.01); *A61B 5/6815* (2013.01); *A61B 5/6817* (2013.01); *A61B 5/6819* (2013.01); *A61B 5/6826* (2013.01); *A61B 5/6838* (2013.01); *A61B 5/721* (2013.01); *A61B 5/7214* (2013.01); *A61B 5/7278* (2013.01); *A61B 5/7282* (2013.01); *A61B 5/742* (2013.01); *A61B 5/7475* (2013.01); *G02B 6/0001* (2013.01); *G06F 19/3418* (2013.01); *H04R 1/105* (2013.01); *H04R 1/1091* (2013.01); *A61B 5/024* (2013.01); *A61B 5/026* (2013.01); *A61B 5/0295* (2013.01); *A61B 5/02405* (2013.01); *A61B 5/02416* (2013.01); *A61B 5/091* (2013.01); *A61B 5/411* (2013.01); *A61B 5/415* (2013.01); *A61B 2560/0242* (2013.01); *A61B 2562/0233* (2013.01)

(56) References Cited

U.S. PATENT DOCUMENTS

| | | |
|---|---|---|
| 4,331,154 A | 5/1982 | Broadwater et al. |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,592,807 A | 6/1986 | Switzer |
| 4,655,225 A | 4/1987 | Dahne et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,957,109 A | 9/1990 | Groeger et al. |
| 5,002,060 A | 3/1991 | Nedivi |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,143,078 A | 9/1992 | Mather et al. |
| 5,226,417 A | 7/1993 | Swedlow et al. |
| 5,237,994 A | 8/1993 | Goldberger |
| 5,348,002 A | 9/1994 | Caro |
| 5,377,100 A | 12/1994 | Pope et al. |
| 5,482,036 A | 1/1996 | Diab et al. |
| 5,492,129 A | 2/1996 | Greenberger |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,853,005 A | 12/1998 | Scanlon |
| 5,904,654 A | 5/1999 | Wohltmann et al. |
| 5,938,593 A | 8/1999 | Quellette |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Nolan et al. |
| 6,013,007 A | 1/2000 | Root et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,283,915 B1 | 9/2001 | Aceti et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |

(56) References Cited

U.S. PATENT DOCUMENTS

| | | |
|---|---|---|
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Römhild |
| 7,034,694 B2 | 4/2006 | Yamaguchi et al. |
| 7,041,062 B2 | 5/2006 | Friedrichs et al. |
| 7,043,287 B1 | 5/2006 | Khalil et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,163,512 B1 | 1/2007 | Childre et al. |
| 7,175,601 B2 | 2/2007 | Verjus et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo et al. |
| 7,341,559 B2 | 3/2008 | Schulz et al. |
| 7,376,451 B2 | 5/2008 | Mahony et al. |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 * | 3/2011 | Shalon ............... A61B 5/0006 600/587 |
| 7,991,448 B2 | 8/2011 | Edgar et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,233,955 B2 | 7/2012 | Al-Ali et al. |
| 8,251,903 B2 | 8/2012 | LeBoeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,679,008 B2 | 3/2014 | Hughes et al. |
| 8,730,048 B2 | 5/2014 | Shen et al. |
| 9,005,129 B2 | 4/2015 | Venkatraman et al. |
| 2001/0049471 A1 | 12/2001 | Suzuki et al. |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0083583 A1 | 5/2003 | Kovtun et al. |
| 2003/0109030 A1 | 6/2003 | Uchida et al. |
| 2003/0181795 A1 | 9/2003 | Suzuki et al. |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0082842 A1 | 4/2004 | Lumba et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2005/0004458 A1 | 1/2005 | Kanayama et al. |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0038349 A1 | 2/2005 | Choi et al. |
| 2005/0043600 A1 | 2/2005 | Diab et al. |
| 2005/0043630 A1 | 2/2005 | Buchert |
| 2005/0058456 A1 | 3/2005 | Yoo |
| 2005/0059870 A1 | 3/2005 | Aceti |
| 2005/0084666 A1 | 4/2005 | Pong et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |

(56) References Cited

U.S. PATENT DOCUMENTS

| | | | |
|---|---|---|---|
| 2005/0187453 A1* | 8/2005 | Petersen | A61B 5/14551 600/336 |
| 2005/0192515 A1 | 9/2005 | Givens et al. | |
| 2005/0196009 A1 | 9/2005 | Boesen | |
| 2005/0203349 A1 | 9/2005 | Nanikashvili | |
| 2005/0203357 A1 | 9/2005 | Debreczeny et al. | |
| 2005/0209516 A1 | 9/2005 | Fraden | |
| 2005/0222487 A1 | 10/2005 | Miller et al. | |
| 2005/0222903 A1 | 10/2005 | Buchheit et al. | |
| 2005/0228244 A1 | 10/2005 | Banet | |
| 2005/0228299 A1 | 10/2005 | Banet | |
| 2005/0240087 A1 | 10/2005 | Keenan et al. | |
| 2005/0258816 A1 | 11/2005 | Zen et al. | |
| 2005/0259811 A1 | 11/2005 | Kimm et al. | |
| 2006/0009685 A1 | 1/2006 | Finarov et al. | |
| 2006/0012567 A1 | 1/2006 | Sicklinger | |
| 2006/0063993 A1 | 3/2006 | Yu et al. | |
| 2006/0064037 A1 | 3/2006 | Shalon et al. | |
| 2006/0084878 A1 | 4/2006 | Banet et al. | |
| 2006/0084879 A1 | 4/2006 | Nazarian et al. | |
| 2006/0122520 A1 | 6/2006 | Banet et al. | |
| 2006/0123885 A1 | 6/2006 | Yates et al. | |
| 2006/0140425 A1 | 6/2006 | Berg et al. | |
| 2006/0142665 A1 | 6/2006 | Garay et al. | |
| 2006/0202816 A1 | 9/2006 | Crump et al. | |
| 2006/0205083 A1 | 9/2006 | Zhao | |
| 2006/0210058 A1 | 9/2006 | Kock et al. | |
| 2006/0211922 A1 | 9/2006 | Al-Ali et al. | |
| 2006/0211924 A1 | 9/2006 | Dalke et al. | |
| 2006/0217598 A1 | 9/2006 | Miyajima et al. | |
| 2006/0224059 A1 | 10/2006 | Swedlow et al. | |
| 2006/0240558 A1 | 10/2006 | Zhao | |
| 2006/0246342 A1 | 11/2006 | MacPhee | |
| 2006/0251277 A1 | 11/2006 | Cho | |
| 2006/0251334 A1 | 11/2006 | Oba et al. | |
| 2006/0252999 A1* | 11/2006 | Devaul | A61B 5/0024 600/300 |
| 2006/0264730 A1 | 11/2006 | Stivoric et al. | |
| 2006/0292533 A1 | 12/2006 | Selod | |
| 2006/0293921 A1 | 12/2006 | McCarthy et al. | |
| 2007/0004449 A1 | 1/2007 | Sham | |
| 2007/0004969 A1 | 1/2007 | Kong et al. | |
| 2007/0015992 A1 | 1/2007 | Filkins et al. | |
| 2007/0021206 A1 | 1/2007 | Sunnen | |
| 2007/0027367 A1 | 2/2007 | Oliver et al. | |
| 2007/0027399 A1 | 2/2007 | Chou | |
| 2007/0036383 A1 | 2/2007 | Romero | |
| 2007/0050215 A1 | 3/2007 | Kil et al. | |
| 2007/0060800 A1 | 3/2007 | Drinan et al. | |
| 2007/0063850 A1 | 3/2007 | Devaul et al. | |
| 2007/0076897 A1* | 4/2007 | Philipp | H04R 1/1041 381/74 |
| 2007/0082789 A1 | 4/2007 | Nissila et al. | |
| 2007/0083092 A1 | 4/2007 | Rippo et al. | |
| 2007/0083095 A1 | 4/2007 | Rippo et al. | |
| 2007/0088221 A1 | 4/2007 | Stahmann | |
| 2007/0093702 A1 | 4/2007 | Yu et al. | |
| 2007/0106167 A1 | 5/2007 | Kinast | |
| 2007/0112273 A1 | 5/2007 | Rogers | |
| 2007/0112598 A1 | 5/2007 | Heckerman et al. | |
| 2007/0116314 A1 | 5/2007 | Grilliot et al. | |
| 2007/0118054 A1 | 5/2007 | Pinhas et al. | |
| 2007/0165872 A1 | 7/2007 | Bridger et al. | |
| 2007/0167850 A1 | 7/2007 | Russell et al. | |
| 2007/0191718 A1 | 8/2007 | Nakamura | |
| 2007/0197878 A1 | 8/2007 | Shklarski | |
| 2007/0197881 A1 | 8/2007 | Wolf et al. | |
| 2007/0213020 A1 | 9/2007 | Novac | |
| 2007/0230714 A1 | 10/2007 | Armstrong | |
| 2007/0233403 A1 | 10/2007 | Alwan et al. | |
| 2007/0265097 A1 | 11/2007 | Havukainen | |
| 2007/0270667 A1 | 11/2007 | Coppi et al. | |
| 2007/0270671 A1 | 11/2007 | Gal | |
| 2007/0293781 A1 | 12/2007 | Sims et al. | |
| 2007/0299330 A1 | 12/2007 | Couronne et al. | |
| 2008/0004536 A1 | 1/2008 | Baxi et al. | |
| 2008/0015424 A1 | 1/2008 | Bernreuter | |
| 2008/0039731 A1 | 2/2008 | McCombie et al. | |
| 2008/0076972 A1 | 3/2008 | Dorogusker et al. | |
| 2008/0081963 A1 | 4/2008 | Naghavi et al. | |
| 2008/0086533 A1 | 4/2008 | Neuhauser et al. | |
| 2008/0096726 A1 | 4/2008 | Riley et al. | |
| 2008/0114220 A1 | 5/2008 | Banet et al. | |
| 2008/0132798 A1 | 6/2008 | Hong et al. | |
| 2008/0141301 A1 | 6/2008 | Azzaro et al. | |
| 2008/0146890 A1 | 6/2008 | LeBoeuf et al. | |
| 2008/0146892 A1 | 6/2008 | LeBoeuf et al. | |
| 2008/0154098 A1 | 6/2008 | Morris et al. | |
| 2008/0154105 A1 | 6/2008 | Lemay | |
| 2008/0165017 A1 | 7/2008 | Schwartz | |
| 2008/0170600 A1 | 7/2008 | Sattler et al. | |
| 2008/0171945 A1 | 7/2008 | Dotter | |
| 2008/0177162 A1 | 7/2008 | Bae et al. | |
| 2008/0200774 A1 | 8/2008 | Luo | |
| 2008/0203144 A1 | 8/2008 | Kim | |
| 2008/0221461 A1 | 9/2008 | Zhou et al. | |
| 2008/0249594 A1 | 10/2008 | Dietrich | |
| 2008/0287752 A1 | 11/2008 | Stroetz et al. | |
| 2009/0005662 A1 | 1/2009 | Petersen et al. | |
| 2009/0006457 A1 | 1/2009 | Stivoric et al. | |
| 2009/0010461 A1 | 1/2009 | Klinghult et al. | |
| 2009/0030350 A1 | 1/2009 | Yang et al. | |
| 2009/0054751 A1 | 2/2009 | Babashan et al. | |
| 2009/0054752 A1 | 2/2009 | Jonnalagadda et al. | |
| 2009/0069645 A1 | 3/2009 | Nielsen et al. | |
| 2009/0082994 A1 | 3/2009 | Schuler et al. | |
| 2009/0088611 A1 | 4/2009 | Buschmann | |
| 2009/0093687 A1 | 4/2009 | Telfort et al. | |
| 2009/0105548 A1 | 4/2009 | Bart | |
| 2009/0105556 A1 | 4/2009 | Fricke et al. | |
| 2009/0112071 A1 | 4/2009 | LeBoeuf et al. | |
| 2009/0131761 A1* | 5/2009 | Moroney, III | A61B 5/0002 600/301 |
| 2009/0131764 A1 | 5/2009 | Lee et al. | |
| 2009/0175456 A1* | 7/2009 | Johnson | H04R 5/04 381/1 |
| 2009/0177097 A1 | 7/2009 | Ma et al. | |
| 2009/0214060 A1 | 8/2009 | Chuang et al. | |
| 2009/0221888 A1 | 9/2009 | Wijesiriwardana | |
| 2009/0227853 A1 | 9/2009 | Wijesiriwardana | |
| 2009/0240125 A1 | 9/2009 | Such et al. | |
| 2009/0253992 A1 | 10/2009 | Van Der Loo | |
| 2009/0253996 A1 | 10/2009 | Lee et al. | |
| 2009/0264711 A1 | 10/2009 | Schuler et al. | |
| 2009/0270698 A1 | 10/2009 | Shioi et al. | |
| 2009/0287067 A1 | 11/2009 | Dorogusker et al. | |
| 2009/0299215 A1 | 12/2009 | Zhang | |
| 2010/0004517 A1 | 1/2010 | Bryenton et al. | |
| 2010/0022861 A1 | 1/2010 | Cinbis et al. | |
| 2010/0045663 A1 | 2/2010 | Chen et al. | |
| 2010/0100013 A1 | 4/2010 | Hu et al. | |
| 2010/0113948 A1 | 5/2010 | Yang et al. | |
| 2010/0168531 A1 | 7/2010 | Shaltis et al. | |
| 2010/0172522 A1 | 7/2010 | Mooring et al. | |
| 2010/0179389 A1 | 7/2010 | Moroney et al. | |
| 2010/0185105 A1 | 7/2010 | Baldinger | |
| 2010/0217102 A1 | 8/2010 | LeBoeuf et al. | |
| 2010/0217103 A1 | 8/2010 | Abdul-Hafiz et al. | |
| 2010/0222655 A1 | 9/2010 | Starr et al. | |
| 2010/0228315 A1 | 9/2010 | Nielsen | |
| 2010/0234714 A1 | 9/2010 | Mercier et al. | |
| 2010/0268056 A1 | 10/2010 | Picard et al. | |
| 2010/0274100 A1 | 10/2010 | Behar et al. | |
| 2010/0274109 A1 | 10/2010 | Hu et al. | |
| 2010/0292589 A1 | 11/2010 | Goodman | |
| 2010/0298653 A1 | 11/2010 | McCombie et al. | |
| 2011/0028810 A1 | 2/2011 | Van Slyke et al. | |
| 2011/0028813 A1 | 2/2011 | Watson et al. | |
| 2011/0081037 A1 | 4/2011 | Oh et al. | |
| 2011/0105869 A1 | 5/2011 | Wilson et al. | |
| 2011/0112382 A1 | 5/2011 | Li et al. | |
| 2011/0130638 A1 | 6/2011 | Raridan, Jr. | |
| 2011/0142371 A1 | 6/2011 | King et al. | |
| 2011/0288379 A1 | 11/2011 | Wu | |

(56) References Cited

U.S. PATENT DOCUMENTS

| | | |
|---|---|---|
| 2012/0030547 A1 | 2/2012 | Raptis et al. |
| 2012/0095303 A1 | 4/2012 | He |
| 2012/0156933 A1 | 6/2012 | Kreger et al. |
| 2012/0179011 A1 | 7/2012 | Moon et al. |
| 2012/0197093 A1 | 8/2012 | LeBoeuf et al. |
| 2012/0277548 A1 | 11/2012 | Burton |
| 2013/0053661 A1 | 2/2013 | Alberth et al. |
| 2013/0072765 A1 | 3/2013 | Kahn et al. |
| 2013/0131519 A1 | 5/2013 | LeBoeuf et al. |
| 2013/0245387 A1 | 9/2013 | Patel |
| 2013/0336495 A1 | 12/2013 | Burgett et al. |
| 2014/0051940 A1 | 2/2014 | Messerschmidt |
| 2014/0052567 A1 | 2/2014 | Bhardwaj et al. |
| 2014/0073486 A1 | 3/2014 | Ahmed et al. |
| 2014/0100432 A1 | 4/2014 | Golda et al. |
| 2014/0127996 A1 | 5/2014 | Park et al. |
| 2014/0219467 A1 | 8/2014 | Kurtz |
| 2014/0236531 A1 | 8/2014 | Carter |
| 2014/0275852 A1 | 9/2014 | Hong et al. |
| 2014/0323880 A1 | 10/2014 | Ahmed et al. |
| 2014/0378844 A1 | 12/2014 | Fei |

FOREIGN PATENT DOCUMENTS

| | | |
|---|---|---|
| DE | 3910749 A1 | 10/1990 |
| EP | 1 297 784 A1 | 4/2003 |
| EP | 1 480 278 A2 | 11/2004 |
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 20030159221 | 6/2003 |
| JP | 2004-513750 A | 5/2004 |
| JP | 2004-283523 | 10/2004 |
| JP | 2007-044203 | 2/2007 |
| JP | 2007-185348 | 7/2007 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 00/24064 | 4/2000 |
| WO | WO 00/47108 A1 | 8/2000 |
| WO | WO 01/08552 A1 | 2/2001 |
| WO | WO 02/17782 A2 | 3/2002 |
| WO | WO 2005/010568 A2 | 2/2005 |
| WO | WO 2005/020121 A1 | 3/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/053146 A1 | 5/2007 |
| WO | WO 2008/141306 A2 | 11/2008 |
| WO | WO 2013/038296 A1 | 3/2013 |
| WO | WO 2014/092932 A1 | 6/2014 |

OTHER PUBLICATIONS

European Search Report, EP Application No. 13863449.8, Oct. 19, 2015, 3 pages.
European Search Report, EP Application No. 14743615.8, Oct. 12, 2015, 3 pages.
European Search Report, EP Application No. 14743839.4, Oct. 12, 2015, 3 pages.
Gibbs et al., "Reducing Motion Artifact in Wearable Bio-Sensors Using MEMS Accelerometers for Active Noise Cancellation," 2005 American Control Conference, Jun. 8-10, 2005, Portland, OR, USA, pp. 1581-1586.
International Preliminary Report on Patentability, PCT/US2014/012940, Jun. 17, 2015, 23 pages.
International Search Report and Written Opinion of the International Searching Authority, corresponding to International Patent Application No. PCT/US2014/012940, Date of Mailing: Oct. 16, 2014, 13 pages.
International Search Report corresponding to International Patent Application No. PCT/US2014/012909, Date of Mailing: May 13, 2014, 3 pages.
Notification Concerning Transmittal of International Preliminary Report on Patentability, PCT/US2014/012909, Jul. 28, 2015.
Wood et al., "Active Motion Artifact Reduction for Wearable Sensors Using Laguerre Expansion and Signal Separation," Proceedings of the 2005 IEEE Engineering in Medicine and Biology, $27^{th}$ Annual Conference, Shanghai, China, Sep. 1-4, 2005, pp. 3571-3574.
"U.S. Army Fitness Training Handbook" by the Department of the Army, 2003, The Lyons Press. p. 17.
Anpo et al. "Photocatalytic Reduction of $Co_2$ With $H_2O$ on Titanium Oxides Anchored within Micropores of Zeolites: Effects of the Structure of the Active Sites and the Addition of Pt" *J. Phys. Chem. B*, 101:2632-2636 (1997).
Bârsan et al. "Understanding the fundamental principles of metal oxide based gas sensors; the example of CO sensing with $SnO_2$ sensors in the presence of humidity" *Journal of Physics: Condensed Matter* 15:R813-R839 (2003).
Bott "Electrochemistry of Semiconductors" *Current Separations* 17(3):87-91 (1998).
Colligan, M. J. et al. in "The psychological effects of indoor air pollution", Bulletin of the New York Academy of Medicine, vol. 57, No. 10, Dec. 1981, p. 1014-1026.
De Paula Santos, U. et al, in "Effects of air pollution on blood pressure and heart rate variability: a panel study of vehicular traffic controllers in the city of Sao Paulo, Brazil", European Heart Journal (2005) 26, 193-200.
Ebert, T et al., "Influence of Hydration Status on Thermoregulation and Cycling Hill Climbing," Med. Sci. Sport Exerc. vol. 39, No. 2, pp. 323-329, 2007.
European Search Report corresponding to European Application No. 07862660.3 dated Apr. 25, 2012; 7 pages.
Falkner et al, "Cardiovascular response to mental stress in normal adolescents with hypertensive parents. Hemodynamics and mental stress in adolescents," *Hypertension* 1979, 1:23-30.
Fleming et al., "A Comparison of Signal Processing Techniques for the Extraction of Breathing Rate from the Photopethysmorgram," World Academy of Science, Engineering and Technology, vol. 30, Oct. 2007, pp. 276-280.
Geladas et al., "Effect of cold air inhalation on core temperature in exercising subjects under stress," The American Physiological Society, pp. 2381-2387, 1988.
Gold, D.R. et al. in "Ambient Pollution and Heart Rate Variability", Circulation 2000, 101:1267-1273.
International Search Report Corresponding to International Application No. PCT/US2012/022634, Date of Mailing: Aug. 22, 2012, 9 pages.
Maomao et al., "Mobile Context-Aware Game for the Next Generation," $2^{nd}$ International Conference on Application and Development of Computer Games ADCOG 2003, p. 78-81.
Martins et al. "Zinc oxide as an ozone sensor" *Journal of Applied Physics* 96(3):1398-1408 (2004).
Maughan, R.J., "Impact of mild dehydration on wellness and on exercise performance," European Journal of Clinical Nutrition, 57, Suppl. 2, pp. S19-S23, 2003.
Maughan et al., "Exercise, Heat, Hydration and the Brain," Journal of the American College of Nutrition, vol. 26, No. 5, pp. 604S-612S, 2007.
Mostardi, R., et al., "The effect of increased body temperature due to exercise on the heart rate and the maximal aerobic power," Europ. J. Appl. Physiol, 33, pp. 237-245, 1974.

(56) References Cited

OTHER PUBLICATIONS

Nakajima et al., "Monitoring of heart and respiratory rates by photoplethyusmography using a digital filtering technique," Med. Eng. Phys., vol. 18, No. 5, Jul. 1996, pp. 365-372.
Saladin et al. "Photosynthesis of $CH_4$ at a $TiO_2$ Surface from Gaseous $H_2O$ and $CO_2$" J. Chem. Soc., Commun. 533-534 (1995).
Shorten et al., "Acute effect of environmental temperature during exercise on subsequent energy intake in active men," Am. J Clin. Nutr. 90, pp. 1215-1221, 2009.
Skubal et al. "Detection and identification of gaseous organics using a $TiO_2$ sensor" Journal of Photochemistry and Photobiology A: Chemistry 148:103-108 (2002)
Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.
Thompson, M.W., "Cardiovascular drift and critical core temperature: factors limiting endurance performance in the heat?" J. Exerc. Sci. Fit, vol. 4, No. 1, pp. 15-24, 2006.
Zhang et al. "Development of Chemical Oxygen Demand On-Line Monitoring System Based on a Photoelectrochemical Degradation Principle" Environ. Sci. Technol., 40(7):2363 -2368 (2006).
FiTrainer "The Only Trainer You Need"; http://itami.com; Downloaded Feb. 26, 2010; © 2008 FiTriainer™; 2 pages.
Communication pursuant to Article 94(3) EPC, European Patent Application No. 12820308.0, Feb. 3, 2016, 5 pages.
Notification of Transmittal of the International Search Report and Written Opinion of the International Search Authority issued May 26, 2016 by the Korean Intellectual Property Office for corresponding International Application No. PCT/US2016/019126.
Notification of Transmittal of the International Search Report and Written Opinion of the International Search Authority issued May 26, 2016 by the Korean Intellectual Property Office for corresponding International Application No. PCT/US2016/019132.
Notification of Transmittal of the International Search Report and the Written Opinion of the International Searching Authority, or the Declaration, PCT/US2015/046079, Dec. 29, 2015.
Communication pursuant to Article 94(3) EPC, European Patent Application No. 13863449.8, Nov. 5, 2015, 7 pages.
Communication pursuant to Article 94(3) EPC, European Patent Application No. 14743615.8, Dec. 23, 2015, 7 pages.
Communication pursuant to Article 94(3) EPC, European Patent Application No. 14743839.4, Dec. 23, 2015, 6 pages.
Extended European Search Report, EP Application No. 16164775.5 Sep. 13, 2016, 7 pages.
Notification of Transmittal of the International Search Report and the Written Opinion of the International Searching Authority, or the Declaration, PCT/US2016/041842, Oct. 21, 2016, 5 pages.
Notification of Transmittal of International Preliminary Report on Patentability, PCT/US2015/041562, Oct. 20, 2016, 14 pages.
Notification of Transmittal of International Preliminary Report on Patentability, PCT/US2015/042636, Oct. 20, 2016, 7 pages.
Notification of Transmittal of International Preliminary Report on Patentability, PCT/US2015/042015, Oct. 20, 2016, 10 pages.
Notification of Transmittal of International Preliminary Report on Patentability, PCT/US2015/042035, Oct. 20, 2016, 8 pages.
Notification of Transmittal of International Preliminary Report on Patentability, PCT/US2015/046079, Oct. 20, 2016, 10 pages.
Asada, et al., "Mobile Monitoring with Wearable Photoplethysmographic Biosensors," IEEE Engineering in Medicine and Biology Magazine, May/Jun. 2003, pp. 28-40.
Bifulco et al., "Bluetooth Portable Device for Continuous ECG and Patient Motion Monitoring During Daily Life," Medicon 2007, IFMBE Proceedings 16, 2007, pp. 369-372.
Brodersen et al., "In-Ear Acquisition of Vital Signs Discloses New Chances for Preventive Continuous Cardiovascular Monitoring," 4th International Workshop on Wearable and Implantable Body Sensor Networks (BSN 2007), vol. 13 of the series IFMBE Proceedings, pp. 189-194.

Celka et al, "Motion Resistant Earphone Located Infrared based Heart Rate Measurement Device," Proceedings of the Second IASTED International Conference on Biomedical Engineering, Feb. 16-18, 2004, Innsbruck, Austria, pp. 582-585.
Communication Pursuant to Article 94(3) EPC, EP 12 739 502.8, Jul. 19, 2016, 7 pages.
Communication Pursuant to Article 94(3) EPC, EP 14 743 615.8, Jul. 19, 2016, 7 pages.
Communication Pursuant to Article 94(3) EPC, EP 14 743 839.4, Jul. 20, 2016, 5 pages.
Comtois et al., "A Wearable Wireless Reflectance Pulse Oximeter for Remote Triage Applications," 2006 IEEE, pp. 53-54.
Comtois, Gary, W., "Implementation of Accelerometer-Based Adaptive Noise Cancellation in a Wireless Wearable Pulse Oximeter Platform for Remote Physiological Monitoring and Triage," Thesis, Worcester Polytechnic Institute, Aug. 31, 2007, 149 pages.
Duun et al., "A Novel Ring Shaped Photodiode for Reflectance Pulse Oximetry in Wireless Applications," IEEE Sensors 2007 Conference, pp. 596-599.
Geun et al., "Measurement Site and Applied Pressure Consideration in Wrist Photoplethysmography," The $23^{rd}$ International Technical Conference on Circuits/Systems, Computers and Communications, 2008, pp. 1129-1132.
Gibbs et al., "Active motion artifact cancellation for wearable health monitoring sensors using collocated MEMS accelerometers," Smart Structures and Materials, 2005: Sensors and Smart Structures Technologies for Civil, Mechanical, and Aerospace Systems, Proc. of SPIE, vol. 5765, pp. 811-819.
Haahr et al., "A Wearable "Electronic Patch" for Wireless Continuous Monitoring of Chronically Diseased Patients," Proceedings of the $5^{th}$ International Workshop on Wearable and Implantable Body Sensor Networks, in conjunction with The $5^{th}$ International Summer School and Symposium on Medical Devices and Biosensors, The Chinese University of Hong Kong, HKSAR, China, Jun. 1-3, 2008, pp. 66-70.
Han et al., "Artifacts in wearable photoplethysmographs during daily life motions and their reduction with least mean square based active noise cancellation method," Computers in Biology and Medicine, 42, 2012, pp. 387-393.
Jiang, Honghui, "Motion-Artifact Resistant Design of Photoplethysmograph Ring Sensor for Driver Monitoring," Thesis, Massachusetts Institute of Technology, Feb. 2004, 62 pages.
Kuzmina et al., "Compact multi-functional skin spectrometry setup," Advanced Optical Materials, Technologies, and Devices, Proc. of SPIE, vol. 6596, 2007, pp. 65960T-1 to 65960T-6.
Lee et al, "Respiratory Rate Detection Algorithms by Photoplethysmography Signal Processing," $30^{th}$ Annual International IEEE EMBS Conference, Vancouver, British Columbia, Canada, Aug. 20-24, 2008, pp. 1140-1143.
Lindberg et al., "Monitoring of respiratory and heart rates using a fibre-optic sensor," Med Biol Eng Comput, Sep. 1992, vol. 30, No. 5, pp. 533-537.
Luprano, Jean, "Sensors and Parameter Extraction by Wearable Systems: Present Situation and Future," pHealth 2008, May 21, 2008, 29 pages.
Lygouras et al., "Optical-Fiber Finger Photo-Plethysmograph Using Digital Techniques," IEEE Sensors Journal, vol. 2, No. 1, Feb. 2002, pp. 20-25.
Maguire et al., "The Design and Clinical Use of a Reflective Brachial Photoplethysmograph," Technical Report NUIM/SS/--/ 2002/04, Submitted Apr. 2002, Signals and Systems Research Group, National University of Ireland, Maynooth, Co. Kildare, Ireland, 13 pages.
Mendelson et al., "Measurement Site and Photodetector Size Considerations in Optimizing Power Consumption of a Wearable Reflectance Pulse Oximeter," Proceedings of the $25^{th}$ Annual International Conference of the IEEE EMBS, Cancun, Mexico, Sep. 17-21, 2003, pp. 3016-3019.
Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.

(56) References Cited

OTHER PUBLICATIONS

Poh et al., "Motion Tolerant Magnetic Earring Sensor and Wireless Earpiece for Wearable Photoplethysmography," IEEE Transactions on Information Technology in Biomedicine, vol. 14, No. 3, May 2010, pp. 786-794.

Renevey et al., "Wrist-Located Pulse Detection Using IR Signals, Activity and Nonlinear Artifact Cancellation," IEEE EMBS, 2001, 4 pages.

Rhee et al., "Artifact-Resistant Power-Efficient Design of Finger-Ring Plethysmographic Sensors," IEEE Transactions on Biomedical Engineering, vol. 48, No. 7, Jul. 2001, pp. 795-805.

Shaltis, Phillip Andrew, Analysis and Validation of an Artifact Resistant Design for Oxygen Saturation Measurement Using Photo Plethysmographic Ring Sensors, Thesis, Massachusetts Institute of Technology, Jun. 2004, 103 pages.

Shin et al., "A Novel Headset with a Transmissive PPG Sensor for Heart Rate Measurement," ICBME 2008, Proceedings 23, 2009, pp. 519-522.

Spigulis et al, "Wearable wireless photoplethysmography sensors," Proc. of SPIE, vol. 6991, 2008, pp. 69912O-1 to 69912O-7.

Takatani et al., "Optical Oximetry Sensors for Whole Blood and Tissue," IEEE Engineering in Medicine and Biology, Jun./Jul. 1994, pp. 347-357.

Vogel et al., "A System for Assessing Motion Artifacts in the Signal of a Micro-Optic In-Ear Vital Signs Sensor," $30^{th}$ Annual International IEEE EMBS Conference, Vancouver, British Columbia, Canada, Aug. 20-24, 2008, p. 510-513.

Vogel et al., "In-Ear Heart Rate Monitoring Using a Micro-Optic Reflective Sensor," Proceedings of the $29^{th}$ Annual International Conference of the IEEE EMBS Cite Internationale, Lyon, France, Aug. 23-26, 2007, pp. 1375-1378.

Wang et al., "Multichannel Reflective PPG Earpiece Sensor With Passive Motion Cancellation," IEEE Transactions on Biomedical Circuits and Systems, vol. 1, No. 4, Dec. 2007, pp. 235-241.

Wang et al., "Reflective Photoplethysmograph Earpiece Sensor for Ubiquitous Heart Rate Monitoring," $4^{th}$ International Workshop on Wearable and Implantable Body Sensor Networks, 2007, vol. 13 of the series IFMBE Proceedings, pp. 179-183.

Wei et al. "A New Wristband Wearable Sensor Using Adaptive Reduction Filter to Reduce Motion Artifact," Proceedings of the $5^{th}$ International Conference on Information Technology and Application in Biomedicine, in conjunction with the $2^{nd}$ International Symposium & Summer School on Biomedical and Health Engineering, Shenzhen, China, May 30-31, 2008, pp. 278-281.

Wood, Levi Benjamin, "Motion Artifact Reduction for Wearable Photoplethysmogram Sensors Using Micro Accelerometers and Laguerre Series Adaptive Filters," Thesis, Massachusetts Institute of Technology, Jun. 2008, 74 pages.

\* cited by examiner

MONITORING APPARATUS AND METHODS FOR MEASURING PHYSIOLOGICAL AND/OR ENVIRONMENTAL CONDITIONS

RELATED APPLICATIONS

This application is a continuation application of pending U.S. patent application Ser. No. 12/711,736, filed Feb. 24, 2010, which claims the benefit of and priority to U.S. Provisional Patent Application No. 61/208,567 filed Feb. 25, 2009, U.S. Provisional Patent Application No. 61/208,574 filed Feb. 25, 2009, U.S. Provisional Patent Application No. 61/212,444 filed Apr. 13, 2009, and U.S. Provisional Patent Application No. 61/274,191 filed Aug. 14, 2009, the disclosures of which are incorporated herein by reference as if set forth in their entireties.

FIELD OF THE INVENTION

The present invention relates generally to health and, more particularly, to health monitoring methods and apparatus.

BACKGROUND OF THE INVENTION

There is growing market demand for personal health monitors, for example, for gauging overall health and metabolism of persons during exercise, athletic training, dieting, and physical therapy. Various physiological information, such as electrocardiogram (ECG) information, electroencephalogram (EEG) information, electrooculography (EOG) information, and other forms of physiological electrical activity, may be useful to monitor during physical activity. However, traditional monitors for measuring this type of information may be bulky, rigid, non-portable, and uncomfortable—generally not suitable for use during physical activity.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the present invention provide novel devices and methods for noninvasively qualifying and/or quantifying physiological information from a subject, such as neurological and cardio-pulmonary information, with various electrodes embedded in an audio headset. According to some embodiments of the present invention, a monitoring apparatus includes a housing configured to be attached to an ear of a subject, and a plurality of electrodes supported by the housing. The electrodes are configured to at least partially contact a portion of the body of the subject when the housing is attached to the ear of the subject, and are configured to detect and/or measure at least one neurological and/or cardiopulmonary function of the subject. Exemplary electrodes that may be utilized include, but are not limited to, electrocardiogram (ECG) electrodes, electroencephalogram (EEG) electrodes, and electrooculography (EOG) electrodes. To ensure good contact with the skin of a subject, the housing may include one or more biasing members or other structures that urge the electrodes into contact with the body of the subject when the housing is attached to the ear of the subject. In addition to electrodes, monitoring apparatus, according to some embodiments of the present invention, may include one or more physiological sensors configured to detect and/or measure physiological information from the subject and/or one or more environmental sensors configured to detect and/or measure environmental conditions in a vicinity of the subject.

In some embodiments of the present invention, a sensor module is included with circuitry that is configured to amplify and/or filter signals produced by the electrodes. In some embodiments, the circuitry comprises a microcontroller. In some embodiments, the sensor module is configured to digitize signals produced by the electrodes. The monitoring apparatus may include a power conditioning component configured to adjust voltage and/or current to the sensor module. A transmitter may be included that is configured to transmit signals processed by the sensor module to a remote device.

In some embodiments, the monitoring apparatus includes a speaker and microphone supported by the housing. The speaker is in electrical communication with an electronic device via an audio output port of the electronic device, and the microphone is in electrical communication with the electronic device via an audio input port of the electronic device. The sensor module modulates and transmits signals produced by the electrodes to the electronic device via the audio input port. In other embodiments, however, the sensor module may be configured to wirelessly transmit signals produced by the electrodes to a remote electronic device.

In some embodiments, circuitry and sensor electrodes are integrated into a sensor control module that processes sensor signals and transmits these signals to another device. In a specific case, the circuitry may comprise a microcontroller, transmitter, sensor electrodes, and additional sensor circuitry.

In some embodiments, the monitoring apparatus is a headset having an ear clip that facilitates attachment of the housing to the ear of a subject. The ear clip may include one or more electrodes configured to at least partially contact a portion of the subject's body when the housing is attached to the ear. In some embodiments, the ear clip may include a pinna cover having one or more electrodes configured to at least partially contact a portion of the ear.

In some embodiments, the monitoring apparatus is an earbud configured to be inserted within an ear of a subject. The earbud includes electrodes configured to at least partially contact a portion of the ear of the subject when the earbud is inserted within the ear of the subject.

In some embodiments, the headset includes two earbuds connected by a supporting member, wherein each earbud is configured to be inserted within a respective ear of a subject. The electrodes may be supported by the supporting member and/or one or both of the earbuds.

According to other embodiments of the present invention, a monitoring apparatus includes a headset configured to be worn by a subject and an electronic device having a user interface. The electronic device may be worn by the subject (e.g., on the body of the subject and/or attached to clothing, etc.). The headset includes a plurality of electrodes (e.g., ECG electrodes, EEG electrodes, EOG electrodes) configured to at least partially contact a portion of the body of the subject when the headset is worn by the subject. The electrodes are configured to detect and/or measure at least one neurological and/or cardiopulmonary function of the subject. The headset also includes a sensor module configured to receive and transmit signals produced by the electrodes to the electronic device for display via the user interface of the electronic device. The sensor module may also be configured to amplify and/or filter signals produced by the electrodes To ensure good contact with the skin of a subject, the headset may include one or more biasing members or other structures that urge the electrodes into contact with the body of the subject when the headset is attached to the ear of the subject. In addition to electrodes, the headset may include one or more physiological sensors configured to detect and/or measure physiological information from the subject and/or one or more environmental sensors configured to detect and/or measure environmental conditions in a vicinity of the subject.

In some embodiments, the headset includes a speaker and a microphone. The speaker is in electrical communication with the electronic device via an audio output port of the electronic device, and the microphone is in electrical communication with the electronic device via an audio input port of the electronic device. The sensor module is configured to modulate and transmit signals produced by the electrodes to the electronic device via the audio input port.

According to other embodiments of the present invention, a monitoring apparatus includes a housing configured to be attached to an ear of a subject, a first electrode supported by the housing and configured to at least partially contact a portion of the body of the subject when the housing is attached to the ear of the subject, an earring configured to be attached to the ear of the subject, and a second electrode supported by the earring and configured to at least partially contact a portion of the ear of the subject when the earring is attached to the ear of the subject. The first and second electrodes are configured to detect and/or measure at least one neurological and/or cardiopulmonary function of the subject. Exemplary electrodes include ECG electrodes, EEG electrodes, EOG electrodes. In some embodiments, the monitoring apparatus includes a sensor module supported by the housing and configured to amplify and/or filter signals produced by the first and second electrodes. In some embodiments, the monitoring apparatus includes a transmitter supported by the housing and configured to transmit signals processed by the sensor module to a remote device.

According to other embodiments of the present invention, a method of monitoring a subject includes detecting neurological and/or cardiopulmonary function information from the subject via electrodes (e.g., ECG electrodes, EEG electrodes, EOG electrodes, etc.) attached to a headset worn by the subject, and transmitting the information to a remote electronic device via an audio input port of the remote electronic device. In some embodiments the headset includes a microphone in electrical communication with the electronic device via an audio input port of the electronic device. Transmitting information to the remote electronic device includes modulating the information and transmitting the information with audio signals produced by the microphone. In some embodiments, transmitting information to the remote electronic device is performed wirelessly.

Because headsets have been adopted for widespread everyday use, embodiments of the present invention provide a convenient and unobtrusive way of monitoring various neurological and cardio-pulmonary functions. Moreover, because the ear region is located next to a variety of "hot spots" for physiological an environmental sensing, including the tympanic membrane, the carotid artery, the paranasal sinus, etc., headsets, according to embodiments of the present invention, are advantageous over other types of monitoring devices configured for other parts of the body. In addition, monitoring apparatus according to embodiments of the present invention can leverage both the bilateral symmetry and asymmetry of the human body. For example, a potential can be measured across the left and right side of the body during the electrical generation of a systolic heart event. For this reason, a net potential may be measured from ear-to-ear during the generation of a heartbeat.

Monitoring apparatus, according to embodiments of the present invention, can utilize commercially available open-architecture, ad hoc, wireless paradigms, such as Bluetooth®, Wi-Fi, or ZigBee. In some embodiments, a small, compact earpiece contains at least one microphone and one speaker, and is configured to transmit information wirelessly to a recording device such as, for example, a cell phone, a personal digital assistant (PDA), and/or a computer. The earpiece contains a plurality of sensors for monitoring personal health and environmental exposure. Health and environmental information, sensed by the sensors can be transmitted wirelessly, in real-time, to a recording device, capable of processing and organizing the data into meaningful displays, such as charts. In some embodiments, an earpiece user can monitor health and environmental exposure data in real-time, and may also access records of collected data throughout the day, week, month, etc., by observing charts and data through an audio-visual display.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

Figure 1:
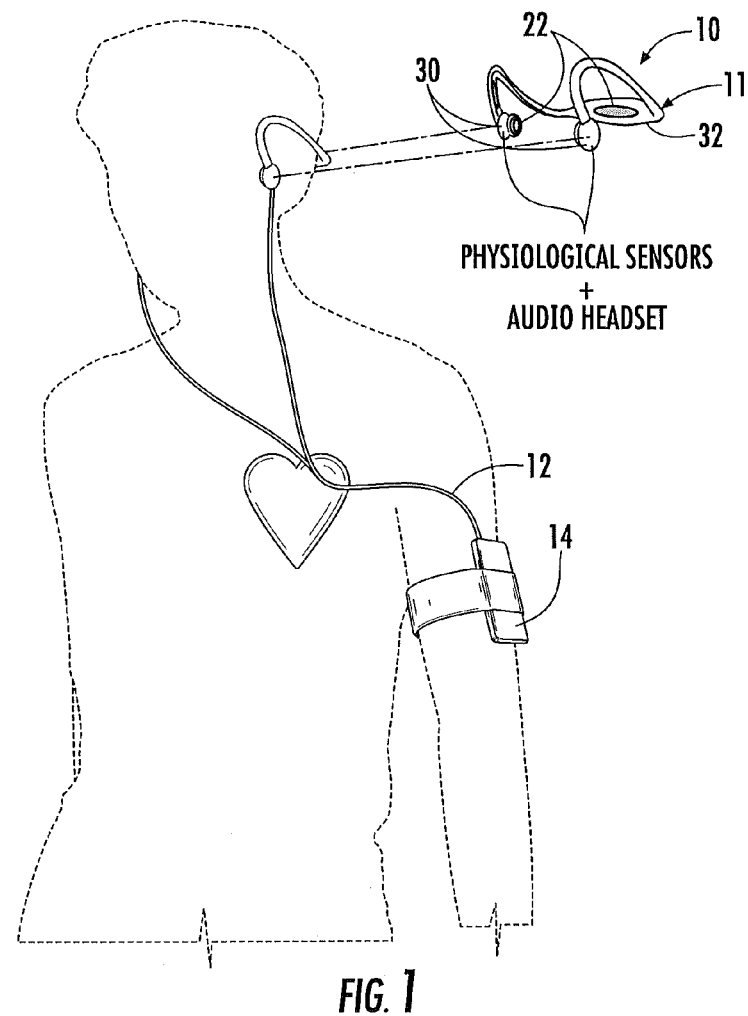
FIG. 1 illustrates a monitoring apparatus, according to some embodiments of the present invention, that includes a headset and a remote electronic device.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "headset" includes any type of device or earpiece that may be attached to or near the ear (or ears) of a user and may have various configurations, without limitation. Headsets, as described herein, may include mono headsets (one earbud) and stereo headsets (two earbuds). The term "earpiece module" includes any type of device that may be attached to or near the ear of a user and may have various configurations, without limitation. The terms "headset" and "earpiece module" may be interchangeable.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements (e.g., physiological sensors, environmental sensors, etc.). For example, "blood health monitoring" includes monitoring blood gas levels, blood hydration, and metabolite/electrolyte levels.

The term "physiological" refers to matter or energy of or from the body of a subject (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "environmental exposure" refers to any environmental occurrence (or energy) to which an individual or group of individuals is exposed. For example, exposure to solar energy, air pollution, temperature, nuclear radiation, humidity, water, etc. may all constitute environmental exposure. A variety of relevant environmental energies are listed elsewhere herein.

The term "body" refers to the body of a subject (human or animal) that may wear a monitoring apparatus, according to embodiments of the present invention.

The term "health" refers generally to the quality or quantity of one or more physiological parameters with reference to an subject's functional abilities.

The term "processor" refers to a device that takes one form of information and converts this information into another form, typically having more usefulness than the original form. For example, in this invention, a signal processor may collect raw physiological or environmental data from various sensors and process this data into a meaningful assessment, such as pulse rate, blood pressure, or air quality. A variety of microprocessors or other processors may be used herein. The terms "signal processor", "processor", "controller", and "microcontroller", as used herein, are interchangeable.

Some embodiments of the present invention arise from a discovery that the ear is an ideal location on the human body for a wearable health and environmental monitor. The ear is a relatively immobile platform that does not obstruct a person's movement or vision. Devices located along the ear can have access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning). The ear is also at or near the point of exposure to: environmental breathable toxicants of interest (volatile organic compounds, pollution, etc.); noise pollution experienced by the ear; and lighting conditions for the eye. Located adjacent to the brain, the ear serves as an excellent location for mounting neurological and electrical electrodes/sensors for monitoring brain activity. Furthermore, as the ear canal is naturally designed for transmitting acoustical energy, the ear provides an optimal location for monitoring internal sounds, such as heartbeat, breathing rate, and mouth motion.

In the following figures, headsets, earpiece modules, and other monitoring apparatus will be illustrated and described for attachment to or near the ear of the human body. However, it is to be understood that embodiments of the present invention are not limited to those worn by humans.

According to some embodiments of the present invention, monitoring apparatus for attachment to or near the ear of a subject include various types of headsets, including wired or wireless headsets. Wired or wireless headsets, such as Bluetooth®-enabled and/or other personal communication headsets, may be configured to incorporate electrodes and physiological and/or environmental sensors, according to some embodiments of the present invention. Bluetooth® headsets are typically lightweight, unobtrusive devices that have become widely accepted socially. Moreover, Bluetooth® headsets may be cost effective, easy to use, and are often worn by users for most of their waking hours while attending or waiting for cell phone calls. Bluetooth® headsets configured according to embodiments of the present invention are advantageous because they provide a function for the user beyond health monitoring, such as personal communication and multimedia applications, thereby encouraging user compliance with monitoring. Exemplary physiological and environmental sensors that may be incorporated into a Bluetooth® or other type of headset include, but are not limited to accelerometers, auscultatory sensors, pressure sensors, humidity sensors, color sensors, light intensity sensors, pressure sensors, noise signal detectors, etc.

Headsets, both mono (single earbud) and stereo (dual earbuds), incorporating low-profile electrodes, sensors and other electronics, according to embodiments of the present invention, offer a platform for performing near-real-time personal health and environmental monitoring in wearable, socially acceptable devices. The capability to unobtrusively monitor an individual's physiology and/or environment, combined with improved user compliance, is expected to have significant impact on future planned health and environmental exposure studies. This is especially true for those that seek to link environmental stressors with personal stress level indicators. The large scale commercial availability of low-cost headset devices can enable cost-effective large scale studies. The combination of monitored data with user location via GPS data can make on-going geographic studies possible, including the tracking of infection over large geographic areas. The commercial application of the various proposed platforms encourages individual-driven health maintenance and promotes a healthier lifestyle through proper caloric intake and exercise.

Accordingly, some embodiments of the present invention combine a personal communications and/or entertainment headset device with one or more electrodes and/or one or more physiological and/or environmental sensors. Embodiments of the present invention are not limited to headsets that communicate wirelessly. In some embodiments of the present invention, headsets configured to monitor an individual's physiology and/or environment may be wired to a device that stores and/or processes data. In some embodiments, this information may be stored on the headset itself.

FIG. 1 illustrates a novel, non-limiting embodiment of a monitoring apparatus 10 for monitoring the physiological properties of a subject. More specifically, the illustrated monitoring apparatus 10 includes a headset 11 which integrates electrodes 22 (FIG. 3) and/or sensors (not shown) for monitoring one or more neurological and/or cardio-pulmonary functions of a subject. The headset 11 can be designed to function as both an audio headset and a physiological monitor while maintaining essentially the same form-factor of an audio headset. The electrodes 22 are configured to at least partially contact a portion of the body of the subject when the headset 11 is attached to the subject. Exemplary electrodes that may be utilized include, but are not limited to, electrocardiogram (ECG) electrodes, electroencephalogram (EEG) electrodes, and electrooculography (EOG) electrodes. To ensure good contact with the skin of a subject, the headset 11 may include one or more biasing members or other structures (not shown) that are configured to urge the electrodes into contact with the body of the subject when the headset 11 is attached to the subject.

In addition to electrodes, the headset 11 may include one or more physiological sensors configured to detect and/or measure physiological information from a subject and/or one or more environmental sensors configured to detect and/or measure environmental conditions in a vicinity of a subject. A physiological sensor can be any compact sensor for monitoring the physiological functioning of the body, such as, but not limited to, sensors for monitoring: heart rate, pulse rate, breathing rate, blood flow, heartbeat signatures, cardio-pulmonary health, organ health, metabolism, electrolyte type and concentration, physical activity, caloric intake, caloric metabolism, metabolomics, physical and psychological stress levels and stress level indicators, physiological and psychological response to therapy, drug dosage and activity (drug dosimetry), physiological drug reactions, drug chemistry in the body, biochemistry, position & balance, body strain, neurological functioning, brain activity, brain waves, blood pressure, cranial pressure, hydration level, auscultatory information, auscultatory signals associated with pregnancy, physiological response to infection, skin and core body temperature, eye muscle movement, blood volume, inhaled and exhaled breath volume, physical exertion, exhaled breath physical and chemical composition, the presence, identity, and concentration of viruses & bacteria, foreign matter in the body, internal toxins, heavy metals in the body, anxiety, fertility, ovulation, sex hormones, psychological mood, sleep patterns, hunger & thirst, hormone type and concentration, cholesterol, lipids, blood panel, bone density, body fat density, muscle density, organ and body weight, reflex response, sexual arousal, mental and physical alertness, sleepiness, auscultatory information, response to external stimuli, swallowing volume, swallowing rate, sickness, voice characteristics, tone, pitch, and volume of the voice, vital signs, head tilt, allergic reactions, inflammation response, auto-immune response, mutagenic response, DNA, proteins, protein levels in the blood, body hydration, water content of the blood, pheromones, internal body sounds, digestive system functioning, cellular regeneration response, healing response, stem cell regeneration response, and the like. Vital signs can include pulse rate, breathing rate, blood pressure, pulse signature, body temperature, hydration level, skin temperature, and the like. A physiological sensor may include an impedance plethysmograph for measuring changes in volume within an organ or body (usually resulting from fluctuations in the amount of blood or air it contains). For example, the wearable monitoring device 10 may include an impedance plethysmograph to monitor blood pressure in real-time.

An external energy sensor, serving primarily as an environmental sensor, can be any compact sensor for monitoring the external environment in the vicinity of the body, such as, but not limited to, sensors for monitoring: climate, humidity, temperature, pressure, barometric pressure, pollution, automobile exhaust, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy (optical radiation, X-rays, gamma rays, microwave radiation, terahertz radiation, ultraviolet radiation, infrared radiation, radio waves, and the like), EMF energy, atomic energy (alpha particles, beta-particles, gamma rays, and the like), gravity, light properties (such as intensity, frequency, flicker, and phase), ozone, carbon monoxide, greenhouse gases, $CO_2$, nitrous oxide, sulfides, airborne pollution, foreign material in the air, biological particles (viruses, bacteria, and toxins), signatures from chemical weapons, wind, air turbulence, sound and acoustical energy (both human audible and inaudible), ultrasonic energy, noise pollution, human voices, animal sounds, diseases expelled from others, the exhaled breath and breath constituents of others, toxins from others, bacteria & viruses from others, pheromones from others, industrial and transportation sounds, allergens, animal hair, pollen, exhaust from engines, vapors & fumes, fuel, signatures for mineral deposits or oil deposits, snow, rain, thermal energy, hot surfaces, hot gases, solar energy, hail, ice, vibrations, traffic, the number of people in a vicinity of the user, the number of people encountered throughout the day, other earpiece module users in the vicinity of the earpiece module user, coughing and sneezing sounds from people in the vicinity of the user, loudness and pitch from those speaking in the vicinity of the user, and the like.

Figure 2:
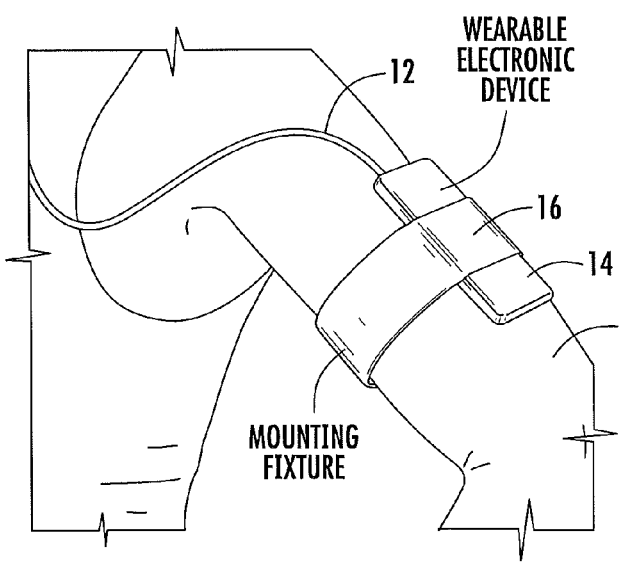
FIG. 2 illustrates the remote electronic device of FIG. 1 attached to the arm of a subject.

As shown in FIG. 1, the headset 11 may connect via a wire 12 to a wearable electronic device 14, though wireless designs are also possible. The wearable electronic device 14 can be any of a variety of wearable devices including, but not limited to, a cellular phone, a smartphone, a digital media player, Walkman®, a personal digital assistant (PDA), a watch, electronic armband, medallion, or the like. In some embodiments, the wearable electronic device can display, audibly, visually, or both, raw or processed information received by the headset 11 via a user interface. The wearable electronic device 14 may be an embedded system or embedded computer. FIG. 2 shows an example of the wearable electronic device 14 worn on the arm of a subject. In the illustrated embodiment, the electronic device 14 is affixed to an arm support 16, such as an armband.

Figure 3:
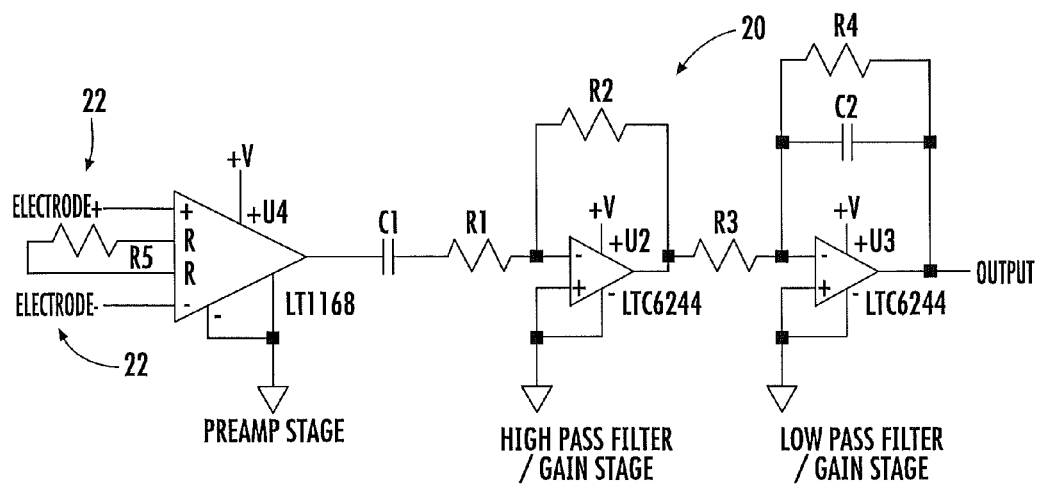
FIG. 3 illustrates a circuit for extracting an ECG signal from the ear of a subject.

FIG. 3 shows an exemplary, nonlimiting electronic circuit 20 for extracting ECG signals from the ear region via electrodes 22 and generating an output. In the illustrated embodiment, multiple gain stages are used to generate a bandpass filter centered in the prime region of an ECG response. Typically, this region will range from 40 Hz to 200 Hz.

Figure 4:
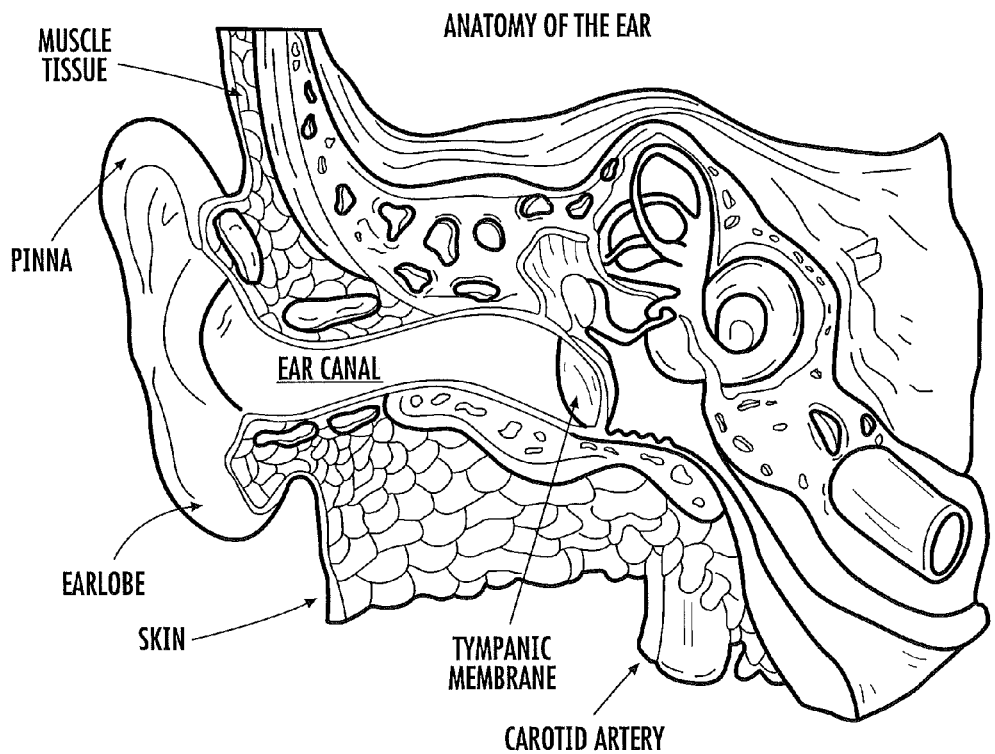
FIG. 4 illustrates the anatomy of a human ear.

FIG. 4 shows a summary of the anatomy of the human ear, where there are several locations suitable for contact with electrodes, such as ECG electrodes. Optimal places include regions where there is a reasonably conductive skin area, such as a region with sweat pores. Nonlimiting skin contact locations for electrodes include: the ear canal, the meatus, the pinna, the scapha, the helix, the tragus, the earlobe, and the periphery surrounding the region where the ear meets the head.

Electrodes 22 utilized in monitoring apparatus, according to embodiments of the present invention, may be composed of any conductive material or materials that are solid or gel-like, including, but not limited to: metals, conductive polymers, conductive gels or sol-gels, alloys, conductive plastics/rubbers, semimetals or semiconductors, and the like. Silver/silver chloride electrodes, carbon rubber, copper, and gold electrodes are just a few examples of electrode materials. Electrodes, according to embodiments of the present invention, need not be passive electrodes. In fact, active electrodes can be employed for impedance matching, impedance reduction, and noise reduction. Active electrodes may employ operational amplifiers, voltage followers, impedance-cancelling circuits, or the like. Furthermore, some electrodes may be configured to measure mostly motion noise, and provide a suitable noise reference for removing noise from an ECG signal. In such case, the noise-detection electrodes may be located in regions without a significant ECG potential drop, such that changes in motion generate a higher potential signal than internal ECG signals from the body. Alternatively, the noise-detection electrodes may be designed to have high impedance to the human body to prevent the pickup of ECG signals, picking up mostly motion-related noise.

Electrodes 22, according to embodiments of the present invention, can be located along any part of a headset touching the skin. Preferably, the electrodes are located in a headset region that is always in contact with the skin during use. Compression fixtures, such as biasing members (e.g., springs, etc.) or other structures, can be used to press the electrodes more closely against the skin. Gels, conductive gels, liquids, lubricants, or the like can be applied to the electrodes to improve the signal-to-noise ratio of signals, such as electrocardiograms, measured. In the illustrated embodiment, the headset 11 includes two earbuds 30 connected by a supporting member 32. Each earbud 30 is configured to be inserted within an ear of a subject. One or more electrodes 22 are supported by the supporting member 32, and one or more electrodes 22 are supported by each earbud 30. In other embodiments, electrodes may be located in only one earbud. In some embodiment, the supporting member 32 may not include electrodes.

In the illustrated embodiment, the supporting member 32 may include one or more biasing members (e.g., a spring) or other structures (not shown) that are configured to urge an electrode 22 into contact with the body of the subject when the headset 11 is worn by the subject. In some embodiments, the supporting member 32 may also help compress the electrodes 22 against the skin to maintain electrode contact. In addition, each earbud 30 having electrodes therein may also include one or more biasing members or other structures that are configured to urge an electrode 22 into contact with the ear of the subject.

In some embodiments, additional electrodes may be integrated with the headset electrodes for a more complete heart monitoring platform. For example, at least one electrode near the leg or ankle may serve as a good ground reference. These additional electrodes may be directly connected to the headset 11 via a wire or may be wirelessly connected to the headset 11.

In another embodiment, at least one electrode 22 may be integrated within the wearable electronic device 14, as this device may be worn in such as way that it is always in contact with human skin S (FIG. 2). In other embodiments, chest electrodes may be integrated within the circuit for assessed multiple chambers and functions of the heart. In each case, the "hub" for collecting, powering, and/or processing this data may be within the headset 11 itself or the wearable electronic device 14. For example, all electrodes 22 may complete a circuit within the wearable electronic device 14 or headset 11.

Figure 5:
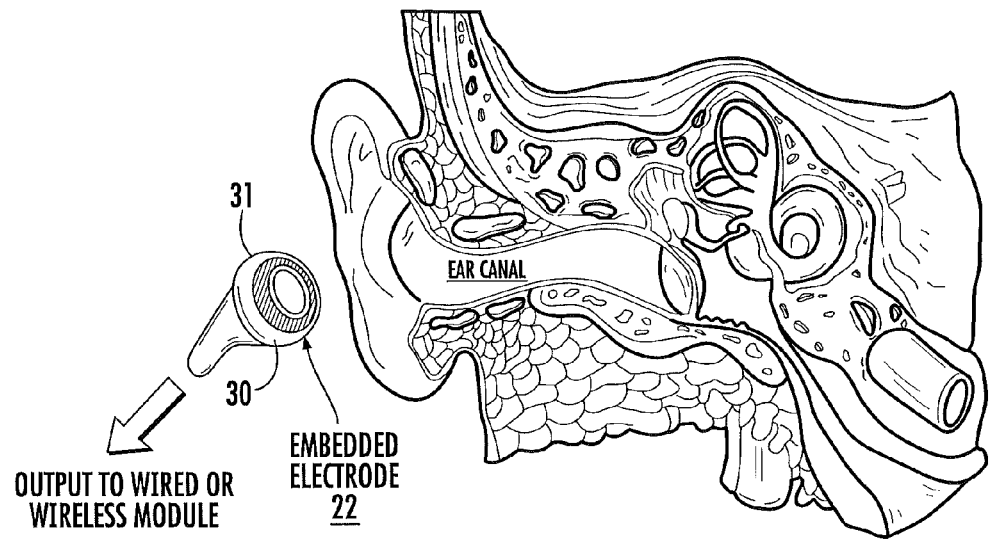
FIG. 5 illustrates a monitoring apparatus in the form of an earbud, according to some embodiments of the present invention, near the ear of a subject.

Referring to FIG. 5, one or more electrodes 22 are located on the outer periphery 31 of the illustrated earbud 30, such that the electrodes 22 are in direct contact with the skin of the mid-to-inner ear region when the earbud 30 is inserted within an ear. The electrodes 22 extend circumferentially around the audio passageway 33 in the illustrated earbud 30. However, in other embodiments, the electrodes 22 may extend circumferentially around only a portion of the audio passageway 33. In some embodiments, a single electrode 22 may be located on an earbud 30. However, in other embodiments, multiple electrodes 22 may be located on an earbud 30. Moreover, multiple electrodes 22 of various shapes and orientations can be located on a single earbud 30.

Figure 6:
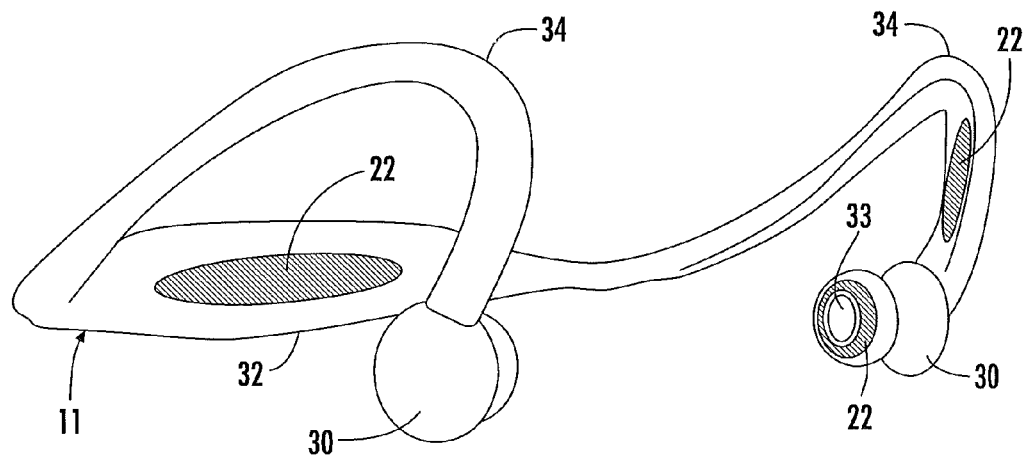
FIG. 6 is a perspective view of a headset with embedded electrodes, according to some embodiments of the present invention.

FIG. 6 is an enlarged view of the headset 11 of FIG. 1 and illustrated electrodes 22 embedded into various locations of the headset 11. In the illustrated embodiment, electrodes 22 are shown embedded in the earbud 30, the ear fixture 34, and a back-of-head supporting member 32. Having more than two electrodes in the headset 11 provides a method of extracting cleaner signals, such as ECG signals, from noise.

Figure 7:
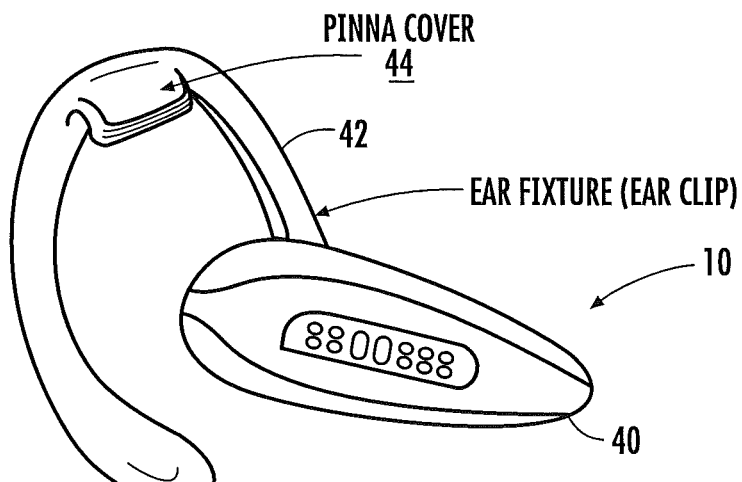
FIG. 7 is a perspective view of a headset monitoring apparatus, according to some embodiments of the present invention.

Referring to FIG. 7, a monitoring apparatus 10, according to other embodiments of the present invention, is illustrated. The illustrated monitoring apparatus 10 includes a housing 40 configured to be attached to an ear of a subject. The illustrated monitoring apparatus 10 also includes an ear clip 42 attached to the housing 40 and that is configured to facilitate attachment of the housing 40 to the ear of a subject. The monitoring apparatus 40 includes a plurality of electrodes (not shown) supported by the housing, and that are configured to at least partially contact a portion of the body of the subject when the housing 40 is attached to the ear of the subject. The electrodes are configured to detect and/or measure at least one neurological and/or cardiopulmonary function of the subject, and may include, for example, ECG electrodes, EEG electrodes, and/or EOG electrodes. In some embodiments, the ear clip 42 may include one or more electrodes configured to at least partially contact a portion of the body of a subject when the housing 40 is attached to the ear of the subject. For example, electrodes may be located in the back (skin-facing) side of the ear clip 42.

In the illustrated embodiment, the ear clip 42 includes a pinna cover 44. The pinna cover 44 may include one or more electrodes configured to at least partially contact a portion of an ear of a subject when the housing 40 is attached to the ear of the subject.

Figure 8:
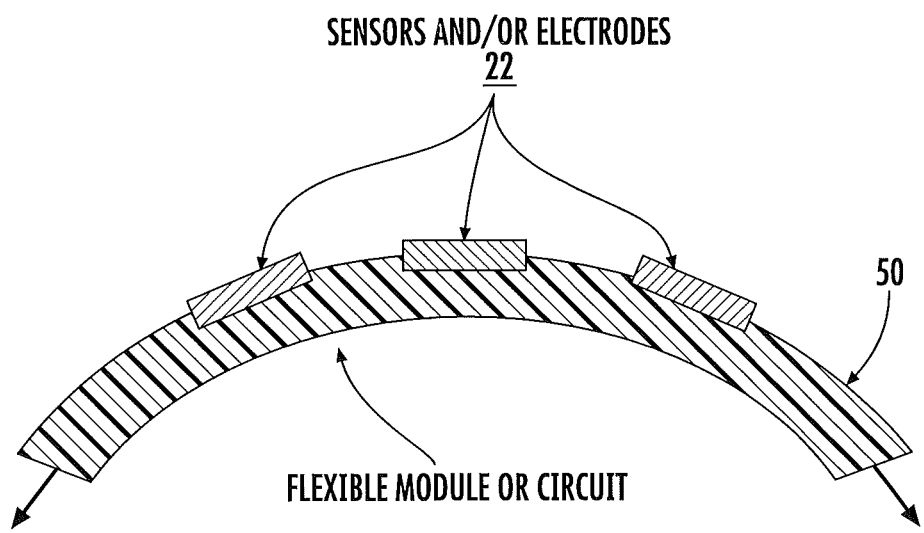
FIG. 8 illustrates a flexible electrode/sensor module that may be utilized within monitoring apparatus according to some embodiments of the present invention.

In some embodiments of the present invention, electrodes 22 may be integrated into flexible modules for a snugger, more comfortable, and/or more reliable electrode configuration. FIG. 8 shows an example of a flexible circuit board 50, according to embodiments of the present invention, that can be made out of virtually any stable flexible material, such as kapton, polymers, flexible ceramics, flexible glasses, rubber, and the like. The flexible material of the flexible circuit board is sufficiently electrically insulating and/or electrochemically inert in comparison with electrodes 22 attached thereto. As with a standard rigid circuit board, a variety of electrodes 22 and/or sensors can be mounted on the flexible circuit board 50, and this board 50 can be integrated into any part of a monitoring apparatus 10. Flexible circuitry can be especially useful for odd-shaped components of an earpiece. In some cases, flexible piezoelectric polymers, such as polyvinylidene fluoride may be useful for measuring body motion, arterial motion, and auscultatory sounds from the body.

Ear jewelry, such as an ear piercing or clip-on jewelry, can also be used to help measure neurological and/or cardiopulmonary functions from a subject, according to some embodiments of the present invention. In such case, electrode wires can be attached to at least one piercing (such as an earring) on each ear of a user, such that the piercing serves as an electrode. Earrings and similar structures may be particularly effective at measuring ECG (and other) signals because they may be highly fixed, localized, and in intimate contact with the skin.

Figure 9:
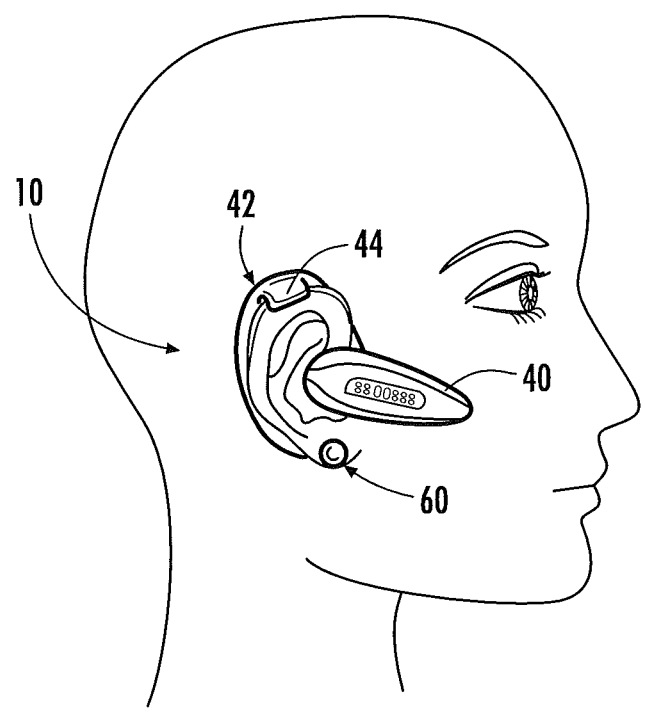
FIG. 9 illustrates a monitoring apparatus in the form of a headset and earring, according to some embodiments of the present invention.

FIG. 9 illustrates a monitoring apparatus 10 that utilizes an earring, according to some embodiments of the present invention. The illustrated monitoring apparatus 10 includes a housing 40 and an earring 60 configured to be attached to an ear of a subject. The housing 40 includes one or more electrodes configured to at least partially contact a portion of the body of the subject when the housing is attached to the ear of the subject. The earring 60 includes one or more electrodes configured to at least partially contact a portion of the ear of the subject when the earring is attached to the ear of the subject. The electrodes supported by the housing 40 and earring 60 are configured to detect and/or measure at least one neurological and/or cardiopulmonary function of the subject. Exemplary electrodes include ECG electrodes, EEG electrodes, EOG electrodes. In some embodiments, the monitoring apparatus 10 includes a sensor module supported by the housing 40 and configured to amplify and/or filter signals produced by the electrodes. In some embodiments, the monitoring apparatus includes a transmitter supported by the housing 40 and configured to transmit signals processed by the sensor module to a remote device.

In the illustrated embodiment of FIG. 9, an ear clip 42 is attached to the housing 40 and includes a pinna cover 44. However, embodiments of the present invention are not limited to the illustrated monitoring apparatus 10. An earring 60 having one or more electrodes may be utilized with various types of headsets, earbuds, etc., without limitation.

Figure 10:
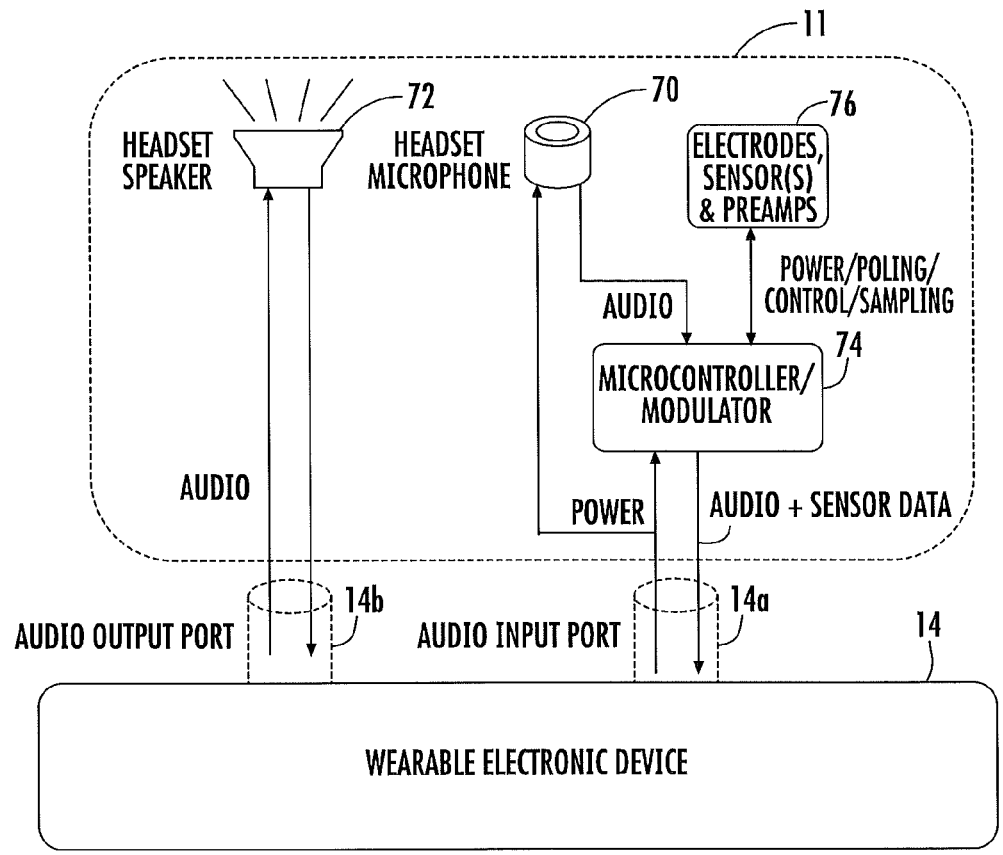
FIGS. 10-12 are block diagrams of monitoring apparatus, according to some embodiments of the present invention.

Referring to FIG. 10, a monitoring apparatus 10 includes an electronic device 14 and headset 11, such as an earbud module, connected to the electronic device 14, and having a plurality of electrodes configured to at least partially contact a portion of the body of a subject when the headset 10 is worn by the subject. The headset 11 includes a plurality of electrodes configured to at least partially contact a portion of the body of the subject when the headset 11 is worn by the subject and configured to detect and/or measure at least one neurological and/or cardiopulmonary function of the subject. The headset 11 may also include one or more physiological/environmental sensors, as described above. The electrodes and sensors, and any associated preamp circuitry, if necessary, are collectively illustrated as 76 in FIG. 10. The headset 11 also includes a speaker 72 and microphone 70. The speaker 72 is in electrical communication with the electronic device 14 via an audio output port 14b of the electronic device 14, and the microphone 70 is in electrical communication with the electronic device 14 via an audio input port 14a of the electronic device 14.

Audio information is passed from the electronic device 14 to the headset speaker 72 and audio information from the microphone 70 is transmitted to electronic device 14 via the respective audio input and output ports 14a, 14b. The headset 11 also includes a microcontroller 74 (or a sensor module including a microcontroller or processor) configured to receive and transmit signals produced by the electrodes/sensors 76 to the electronic device for display via a user interface associated with the electronic device 14. The microcontroller 74 is configured to modulate and transmit signals produced by the electrodes/sensors 76 to the electronic device 14 via the audio input port 14b. The sensor data may be modulated by the microcontroller/modulator 74 in such a way that it does not interfere with the audio signal and/or in such a way that it can be easily demodulated by the electronic device 14. Modulation of an electrode signal, such as an ECG signal, can be achieved through an analog modulation technique and/or a digital modulation technique, including, but not limited to amplitude modulation, frequency modulation, phase modulation, phase-shift keying, frequency-shift keying, amplitude-shift keying, quadrature amplitude modulation, continuous phase modulation, wavelet modulation, trellis coded modulation, orthogonal frequency division multiplexing, or the like.

The illustrated embodiment of FIG. 10 is advantageous because it allows the electrodes and sensors to be sampled through the 4-wire audio input/output ports 14a, 14b of the electronic device 14. In addition, it allows multiple sensors to be integrated into the same headset or earbud module with minimal hardware reconfiguration. In some wearable devices, additional input/output ports are not accessible for external hardware not developed by the original manufacturer. In such case, embodiments of the present invention exploit the analog audio input/output ports of the electronic device without disturbing the audio performance of the headset for both audio input (to a headset speaker) and audio output (from a headset microphone).

The microcontroller 74 may digitize both the audio and sensor signals for digital modulation. In another embodiment, this digitally modulated signal may then be converted to an analog modulated signal, preferably an audio modulated signal, via the microcontroller 74 using a digital-to-analog converter (DAC). In this case, an analog signal, as opposed to a digital signal, would pass through the audio input port 14a of the electronic device 14. In other embodiments, the microcontroller 74 may digitize sensor information into a buffer in memory, convert the buffered digital information to an analog signal (via a DAC), and send the analog signal to a modulator for combining the analog microphone audio signal with the analog sensor signal. Converting digital signals back to analog signals may be beneficial because the audio input of the wearable electronic device may not be suited for digital information. The modulator itself may be part of the microcontroller, a separate chip, or a separate circuit.

In some cases, the audio input port 14a of the electronic device 14 may not supply the right level of voltage and/or current. In such case, a power conditioning chip and/or circuit can be implemented to raise or lower the voltage. For example, a voltage multiplier chip may be used to increase the voltage from the audio input port 14a. In some cases, the microcontroller 74 itself may have onboard power conditioning such that additional circuitry is not required.

Although the embodiment of FIG. 10 shows the headset 11 wired to an electronic device 14, it should be understood that wireless versions can also be implemented. The audio input and output lines to and from the headset 11 can be connected to a wireless chip, for generating a wireless signal to be received by a wireless receiver in the wearable electronic device. Examples of wireless chips include, but are not limited to, Bluetooth® chips, ZigBee chips, WiFi chips, and the like. In some cases, the microcontroller 74 itself can be the internal microcontroller of the wireless chip, for a heavily integrated solution. A specific example of this is the Bluecore processor of the Bluecore chip. For even further integration, the entire processing, wireless interface, and modulating electronics can be integrated into an ASIC (application-specific integrated circuit).

In some cases, the analog sensor signals, such as the electrode and/or sensor signals, may pass through the audio input port 14a directly, to be processed further via an embedded computer in the electronic device 14. In such case, the electrode/sensor signals may be processed mostly or entirely by the electronic device 14.

The output of electrodes/sensors 76 can be passed to the electronic device 14 through a wired or wireless configuration. For example, in the wireless configuration, the amplified output from an electrode/sensor 76 can be passed to a wireless processing module, where the wireless processing module can be embedded in the headset 11, as with a Bluetooth® headset. To communicate with the wireless headset 11, the electronic device 14, or associated modules attached to the electronic device 14, are capable of receiving and processing the wireless signal from the wireless headset. Suitable wireless protocols include, but are not limited to, Bluetooth®, ZigBee, WiFi, radio, and several others. In a wired version, the amplified output from an electrode/sensor 76 can be processed in a module embedded in the headset 11, where the resulting signal is passed through one or more wires to the electronic device 14.

In some embodiments of the present invention, an electronic device 14 may contain one or more port(s), capable of wired or wireless contact with a headset 11. These ports are suitable for receiving analog or digitized data from the headset and/or transmitting analog or digitized signals from the electronic device 14 to the headset 11. Examples of such ports include, but or not limited to, Bluetooth® dongles, ZigBee dongles, USB, UART, RS232, Firewire®, optical, proprietary, or other port. In some embodiments, the ports may be connected directly to separate modules that connect in a wired or wireless fashion with a headset 11. These modules may be necessary for conditioning the signals or power levels received by or transmitted to the headset. A Bluetooth®, ZigBee, level translator, mating connector, or DTMF dongle is one example of such a module. These modules may contain signal processing circuitry or components to condition the signals.

As shown in FIG. 10, the signals entering the electronic device 14, sent from the headset 11, may be composed of modulated audio+sensor information. The electronic device 14, serving as an embedded computer, can digitize, demodulate, process, and manipulate this signal internally. The end result is a pure (or mostly pure) audio signal and a separate sensor signal. Through a user interface, such as a graphical user interface (GUI) of the electronic device 14, processed electrode/sensor information can be displayed visually and/or audibly to the user in a colorful and engaging display. The end result is real-time active health and fitness feedback for the headset wearer, while he/she enjoys audio at the same time. In some cases, the feedback may be related through the audio headset itself. ECG signals, EEG signals. EOG signals, core body temperature, physical activity, pulse rate, breathing rate, and other physiological information can be processed by the embedded computer into meaningful assessments such as calories burned, $VO_2$max, cardiovascular health, and the like.

In some embodiments of the present invention, additional sensors are embedded into the headset 11 for monitoring additional physiological information, noise information (such as motion noise information), and/or environmental exposures of the headset wearer. In such case, an onboard microcontroller 74 (or sensor module comprising a microcontroller or processor) can be used to coordinate the collection, modulation, and transmission of various sensor information. The bi-directional arrow in FIG. 10 between the microcontroller 74 and the electrodes/sensors 76 indicates that bidirectional communication may be employed. In a specific embodiment, the sensors are connected in a serial bus, such as an I2C bus, for poling each sensor and synchronizing the output signal to the wearable electronic device.

The electrodes, as well as additional sensors, can be embedded into a standard audio headset through a variety of processes, including, but not limited to: molding, screen printing, prefabrication, embedded design, encapsulation, or the like. In the specific case of molding, a plastic mold may be generated to fit the desired electrode geometry. As the electrode may be integrated into an electronic module, the mold may be designed to fit the entire module. The module may include all electronic components, including the audio speaker or audio microphone. Screen printing conductive electrodes can be useful for printing over existing, prefabricated headsets. In some cases, the metal enclosures from the headsets or headset speakers themselves can serve as an electrode. In the case of wired headsets, additional wires may be added to connect with ports in the wearable electronic device.

The electrodes described herein can also be used to measure the EEG and/or EOG of a person wearing the headset. Extracting EEG and EOG signals in the midst of ECG signals can be achieved using several methods. One method is to place the electrodes in locations closest to a region of interest. For example, integrating EOG sensors in a headset fixture close to the eyes would improve the response to the EOG. Another method is to integrate multiple electrodes at various regions on a single earpiece. As a specific example, having two separate electrodes in each earpiece of a stereo headset would provide a way of differentiating EOG, EEG, and ECG signals. This is because the localized potential between the two closely space electrodes in a single earbud can be more indicative of localized EOG and EEG events, whereas the more distal potential between electrodes in separate earbuds can be more indicative the ECG response.

Figure 12:
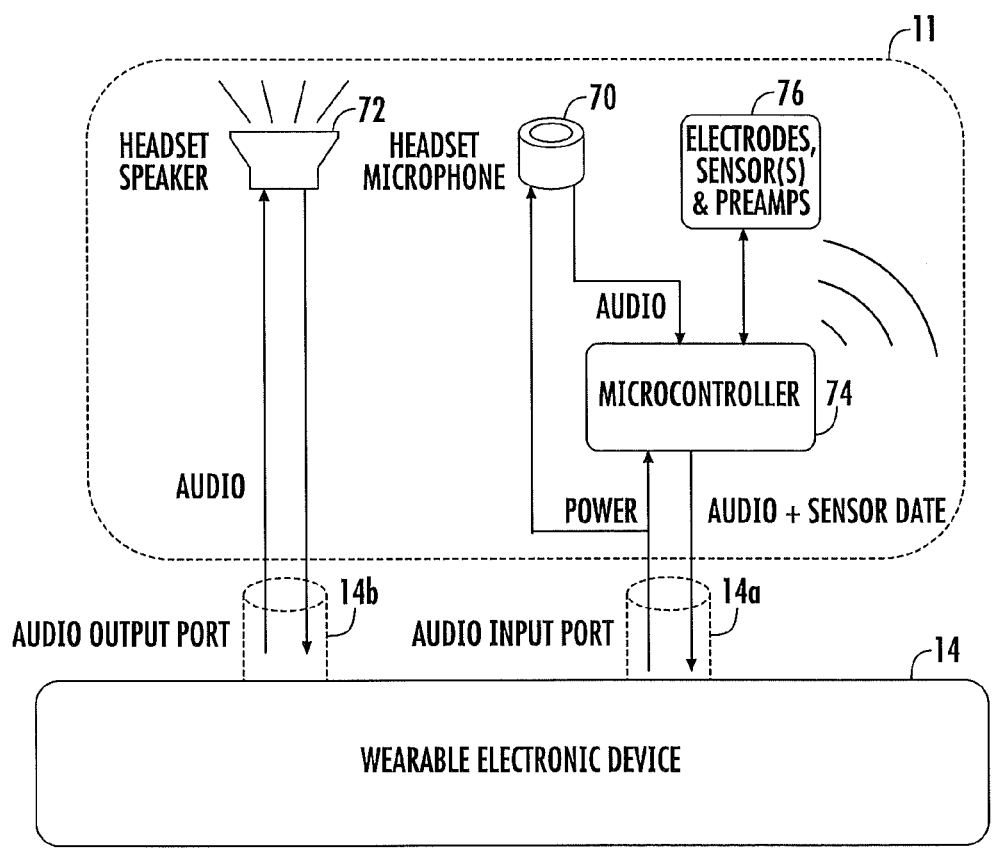

Although FIG. 10 illustrates the headset 11 wired to an electronic device 14, it should be understood that wireless versions can also be implemented, according to some embodiments of the present invention. For example, the audio input and output lines to and from the headset 11 can be connected to a wireless chip, for generating a wireless signal to be received by a wireless receiver in the electronic device 14. Examples of wireless chips include, but are not limited to, Bluetooth® chips, ZigBee chips, WiFi chips, and the like. In some embodiments, the microcontroller 74 itself can be the internal microcontroller of the wireless chip, for a heavily integrated solution. A specific example of this is the Bluecore processor of the Bluecore chip. For even further integration, the entire processing, wireless interface, and modulating electronics can be integrated into an ASIC (application-specific integrated circuit). The microcontroller 74 in the illustrated embodiment of FIG. 12 may integrate the sensor, processor, and wireless electronics to communicate with a remote device. In this way, the phone jack may power the microcontroller and the microcontroller may wirelessly communicate with a remote device.

Figure 11:
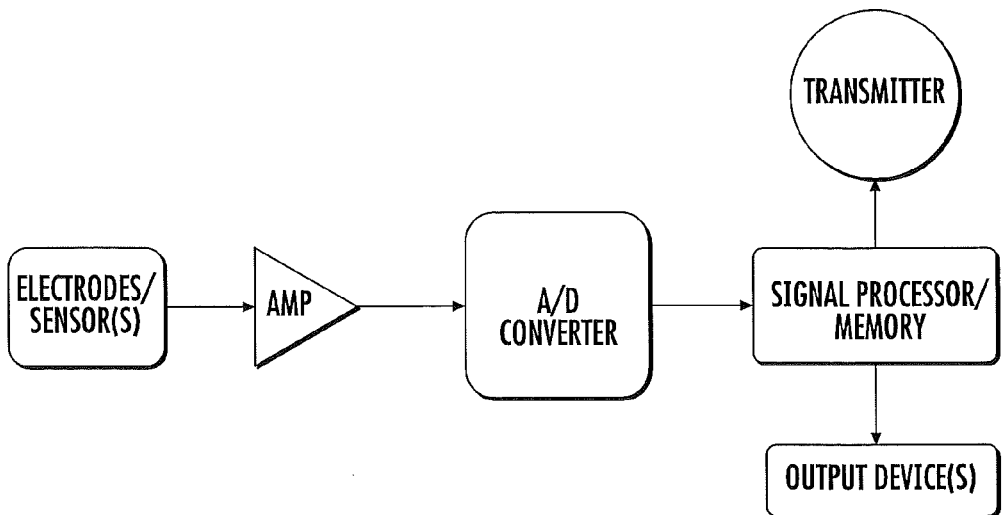

FIG. 11 is a block diagram illustrating that circuitry for sensing and processing electrical signals from the body of a subject may be integrated into a sensor module. For example, the sensor module represented by FIG. 11 may replace the microcontroller 74 illustrated in FIGS. 10 and 12, according to some embodiments of the present invention. As illustrated in FIG. 11, a sensor module, according to embodiments of the present invention, may include circuitry for power conditioning, signal conditioning, ND and D/A conversion, wireless transmission, controls, and the like. For example, in some embodiments, the sensor module may comprise a microcontroller, sensor, and a wireless transmitter.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A removable audio headset connected to a wearable electronic device via an audio port of the wearable electronic device, the headset comprising:

at least one earbud;

at least one physiological sensor powered by a power supply of the wearable electronic device via the audio port of the wearable electronic device, wherein the at least one physiological sensor is configured to detect physiological information from a person wearing the headset and is configured to produce an electrical signal containing the physiological information;

at least one microphone powered by the power supply of the wearable electronic device via the audio port of the wearable electronic device, wherein the microphone is configured to produce an audio signal containing audio information responsive to a verbal communication by the person;

power conditioning circuitry configured to condition the power received from the power supply of the wearable electronic device and to adjust voltage and/or current supplied to the at least one physiological sensor; and modulation circuitry powered by the power supply of the wearable electronic device, wherein the modulation circuitry is configured to modulate the electrical signal produced by the at least one physiological sensor and the audio signal produced by the at least one microphone to create a modulated signal comprising both the audio information and the physiological information, wherein the modulation circuitry is configured to transmit the modulated signal via the audio port of the wearable electronic device, and wherein the wearable electronic device includes demodulating circuitry configured to receive and to demodulate the modulated signal.

2. The audio headset of claim 1, wherein the at least one physiological sensor is configured to be integrated within the earbud.

3. The audio headset of claim 1, wherein the headset further comprises wireless communication circuitry configured to be powered by the power supply of the wearable electronic device, wherein the wireless communication circuitry is further configured to transmit data from the at least one physiological sensor to a remote device.

4. A removable audio headset connected to a wearable electronic device via an audio port of the wearable electronic device, the headset comprising:

at least one earbud;

at least one physiological sensor powered by a power supply of the wearable electronic device via the audio port of the wearable electronic device, wherein the at least one physiological sensor is configured to detect physiological information from a person wearing the headset and is configured to produce an electrical signal containing the physiological information;

wireless communication circuitry; and at least one processor configured to receive the electrical signal from the at least one physiological sensor and to transmit the electrical signal to the wearable electronic device via the wireless communication circuitry; and power conditioning circuitry in electrical communication with the audio port, wherein the power conditioning circuitry is configured to condition the power received from the power supply of the wearable electronic device and to adjust voltage and/or current supplied to the at least one physiological sensor and to the wireless communication circuitry.

* * * * *

UNITED STATES PATENT AND TRADEMARK OFFICE
CERTIFICATE OF CORRECTION

PATENT NO. : 9,750,462 B2
APPLICATION NO. : 14/166365
DATED : September 5, 2017
INVENTOR(S) : LeBoeuf et al.

Page 1 of 1

It is certified that error appears in the above-identified patent and that said Letters Patent is hereby corrected as shown below:

In the Specification

Column 16, Line 33: Please correct "ND" to read -- A/D --

Signed and Sealed this
Tenth Day of July, 2018

Andrei Iancu
*Director of the United States Patent and Trademark Office*